(12) United States Patent
Warner et al.

(10) Patent No.: US 9,522,102 B2
(45) Date of Patent: *Dec. 20, 2016

(54) FORMULATION AND PROCESSES FOR HAIR COLORING

(71) Applicants: John C. Warner, Wilmington, MA (US); Laura Muollo, Dracut, MA (US); Amie Stewart, Reading, MA (US)

(72) Inventors: John C. Warner, Wilmington, MA (US); Laura Muollo, Dracut, MA (US); Amie Stewart, Reading, MA (US)

(73) Assignee: WARNER BABCOCK INSTITUTE FOR GREEN CHEMISTRY, LLC, Wilmington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/481,842

(22) Filed: Sep. 9, 2014

(65) Prior Publication Data

US 2016/0184197 A1  Jun. 30, 2016

Related U.S. Application Data

(63) Continuation-in-part of application No. 14/053,524, filed on Oct. 14, 2013, now Pat. No. 8,828,100.

(51) Int. Cl.
| | | |
|---|---|---|
| *A61Q 5/10* | (2006.01) | |
| *B65D 69/00* | (2006.01) | |
| *A61K 8/19* | (2006.01) | |
| *A61K 8/81* | (2006.01) | |
| *A61K 8/22* | (2006.01) | |
| *A61K 8/44* | (2006.01) | |
| *A61K 8/41* | (2006.01) | |

(52) U.S. Cl.
CPC . *A61K 8/19* (2013.01); *A61K 8/22* (2013.01); *A61K 8/415* (2013.01); *A61K 8/445* (2013.01); *A61K 8/8147* (2013.01); *A61Q 5/10* (2013.01); *A61K 2800/4324* (2013.01); *A61K 2800/884* (2013.01)

(58) Field of Classification Search
CPC .............. A61Q 5/10; A61K 8/22; A61K 8/19; A61K 8/29; A61K 8/92; A61K 2800/88
USPC ................................................ 8/405; 206/568
See application file for complete search history.

(56) References Cited

U.S. PATENT DOCUMENTS

| | | | | |
|---|---|---|---|---|
| 4,904,274 | A * | 2/1990 | Schultz | ................... A61Q 5/065 8/406 |
| 8,828,100 | B1 * | 9/2014 | Warner | ..................... A61Q 5/10 8/405 |
| 2009/0119852 | A1 * | 5/2009 | Marsh | ...................... A61K 8/34 8/408 |

\* cited by examiner

*Primary Examiner* — Eisa Elhilo
(74) *Attorney, Agent, or Firm* — The Patent Practice of Szmanda & Shelnut, LLC; Charles R. Szmanda; James G. Shelnut

(57) ABSTRACT

Disclosed and claimed herein are a composition and a kit for coloring keratin fibers, and processes of their use. The composition includes a catechol-based color precursor.

17 Claims, No Drawings

FORMULATION AND PROCESSES FOR HAIR COLORING

REFERENCE TO PRIOR FILED APPLICATION

The present application is a Continuation-In-Part of U.S. application Ser. No. 14/053,524, filed Oct. 14, 2013 (now U.S. Pat. No. 8,828,100), which prior filed application is incorporated herein by reference in its entirety.

FIELD OF THE INVENTION

The present invention is in the field of kits, compositions, and processes for the coloration of keratin fibers.

BACKGROUND

Materials have been dyed and colored for thousands of years. While natural substances have historically been used to color most materials, these substances are often unable to permanently dye many types of materials. There is, therefore, a large demand for synthetic dye formulations that permanently color a material, including natural and artificial fibers, among many other beneficial uses. One of the largest markets for permanent dye formulations is the hair coloring market.

Hair is made of three layers: the outer layer called the cuticle, the sub-layer called the cortex, and an inner hollow shaft called the medulla. The cortex contains varying amounts of two natural color pigments, eumelanin and pheomelanin, that determine a person's hair color. Eumelanin is a dark pigment, and is responsible for brown and black color. Pheomelanin produces blonde and red. Thus the cortex of a black hair will contain densely packed granules of eumelanin pigment. An absence of pigment results in gray hair.

The permanency, or level of hair coloration, is dependent on the degree of penetration of colorant molecules into the hair. Temporary colorants merely coat the surface of the hair on the cuticle. Because the colorant does not penetrate the hair cuticle, it is easily washed out. Semi-permanent colorants, such as dyes, add color to the cuticle layer, but do not bind to the hair protein itself. When the hair is washed, the cuticle layer opens, allowing some color to escape.

To permanently change the color of hair, the coloring ingredients must be able to penetrate the outer layer of the hair called the cuticle, which consists of tightly packed, overlapping, colorless cells. Most permanent hair color products contain a developer and an alkalizing agent. The developer is usually an oxidizing agent such as hydrogen peroxide in water or a cream lotion, and the alkalizing agent is most often ammonia or ammonia substitutes such as organic amines. Alkalizing agents cause the hair to swell and thus allow the pigment to penetrate the hair cuticle deep enough to reach and replace the natural melanin.

To achieve hair coloring, both semi-permanent and permanent colorant formulations often involve the oxidation of toxic precursor molecules such as phenylenediamine or 2,5-diaminotoluene. Typical formulations involve hydrogen peroxide and ammonia, or even harsher chemicals such as lead acetate. Lead acetate is a neurotoxin that can be fatal if absorbed through the skin in high enough amounts. Several studies have suggested that the chemicals found in synthetic hair colorants, including ammonia, aromatic diamine color precursors, lead, organic solvents and coal tar derivatives, are either toxic or can have undesirable side-effects such as hair loss, burning, redness, itchy skin, swelling, or breathing trouble. Moreover, most hair coloring formulations employ oxidizing agents in high concentration. As a result, many people decide to forego hair colorants to avoid exposure to the chemicals found in the coloring compositions.

Although there are some natural formulations that employ compounds found in nature, they tend to be inconsistent and, often, provide only temporary results.

Some coloring processes can take upwards of 60 minutes to reach the desired level of coloration. To speed up the process metal ion catalysts can be used. The hair is either first treated with a metal ion composition followed by the color precursor materials or the hair is treated with a composition containing both the metal ions and the color precursor materials.

Most coloring processes rely on coloring the fibers, such as hair, to a particular pre-determined color such as brown, black, blonde, red, and various shades in between. There are no effective processes that are designed to return a person's hair to its original natural shade or a close proximity. In effect the pre-determined color process is a guess as to what the hair will look like when finally colored. Thus there is a long felt desire and need for hair coloring kits, compositions, processes and methods which will reproduce as closely as possible a person's hair to its original color and shade.

As a result, there is a continued need for coloring compositions that use natural compounds rather than synthetic or toxic chemicals to color hair permanently. Additionally, there is a continued demand for efficient and environmentally-friendly compositions and processes for coloring hair either permanently or semi-permanently that do not involve the use of organic solvents or organic bases. Further, there is a continued demand for hair dye formulations that use oxidizing agents in lower concentration.

BRIEF DESCRIPTION

It has surprisingly been found that the compositions of the current disclosure, and the processes of using them on keratin fibers, allow the users' hair to essentially return to its original, natural color and shade.

In an aspect, there is disclosed a system for coloring keratin fibers comprising a first composition comprising at least one catechol-based color precursor or a pharmaceutically acceptable salt thereof and at least one pharmaceutically acceptable base and a second composition comprising at least one pharmaceutically acceptable base; wherein at least one of the compositions further comprise at least one oxidizing agent and at least one of a metal salt chosen from Fe(III), Fe(II), Co (II), Co(III), Ag(I), Ti(II), Cu(I), Cu(II), Cr(II), Cr(III), Mo(II), Mo(III), Ni(II), Ni(III), Mn(II) and Zn(II).

In another aspect, there is disclosed a kit for coloring keratin fibers comprising the ingredients of at least one catechol-based color precursor or a pharmaceutically acceptable salt thereof, at least one pharmaceutically acceptable base, at least one oxidizing agent, at least one abrasive and at least one of a metal salt chosen from Fe(III), Fe(II), Co (II), Co(III), Ag(I), Ti(II), Cu(I), Cu(II), Cr(II), Cr(III), Mo(II), Mo(III), Ni(II), Ni(III), Mn(II) and Zn(II) and optionally a thickening agent.

In another aspect, there is disclosed a kit for coloring keratin fibers comprising a first package comprising an oxidizing agent, a second package comprising at least one catechol-based color precursor or a pharmaceutically acceptable salt thereof, and at least one pharmaceutically acceptable base, and a third package comprising at least one pharmaceutically acceptable base, and at least one of a metal salt chosen from Fe(III), Fe(II), Co (II), Co(III), Ag(I), Ti(II), Cu(I), Cu(II), Cr(II), Cr(III), Mo(II), Mo(III), Ni(II), Ni(III), Mn(II) and Zn(II) or at least one catechol-based color precursor.

In another aspect, there is disclosed a process for coloring keratin fibers comprising the steps of a) combining at least a portion of a first package comprising an oxidizing agent with at least a portion of a second package comprising at least one catechol-based color precursor or a pharmaceutically acceptable salt thereof, and at least one pharmaceutically acceptable base, and applying the combination to the keratin fibers, and b) combining at least a portion of a second package comprising at least one catechol-based color precursor or a pharmaceutically acceptable salt thereof, and at least one pharmaceutically acceptable base with at least a portion of a third package comprising at least one pharmaceutically acceptable base, and at least one of a metal salt chosen from Fe(III), Fe(II), Co (II), Co(III), Ag(I), Ti(II), Cu(I), Cu(II), Cr(II), Cr(III), Mo(II), Mo(III), Ni(II), Ni(III), Mn(II) and Zn(II) or at least one catechol-based color precursor and applying to the keratin fibers.

DETAILED DESCRIPTION

Herein, the conjunction "or" is not intended to be exclusive unless otherwise noted. For example, the phrase "or alternatively" is intended to be exclusive. Further, when used in connection with chemical substitution at a specific position, the conjunction "or" is intended to be exclusive. As used herein, the adjective "exemplary" is used simply to point to an example and is not meant to indicate preference.

As used herein the term colorant is intended to mean dyes, pigments and combinations thereof, and the term coloring is intended to mean dyeing, pigmenting and combinations thereof.

By the term "pharmaceutically acceptable salt" is intended salts with pharmaceutically acceptable acids or bases. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the catechol-based precursor, or separately by reacting the free base function with a suitable organic acid. Examples of pharmaceutically acceptable salts include, but are not limited to, nontoxic acid addition salts such as salts of an amino group formed with inorganic acids such as hydrochloric acid, hydrobromic acid, phosphoric acid, sulfuric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Pharmaceutically acceptable salts of carboxylates and other oxo-acids can be formed with cationic species such as alkali or alkaline earth metal ions including sodium, lithium, potassium, calcium, magnesium, and the like. Further, pharmaceutically acceptable salts include, when appropriate, nontoxic ammonium, quaternary ammonium, and amine cations as well as natural product cations such as choline and acetyl choline and the like. Anionic counterions include halides, hydroxide, carboxylate, sulfate, phosphate, nitrate, alkyl (having from 1 to 6 carbon atoms) sulfonate and aryl sulfonate.

As used herein "keratin fibers" may be human keratinous fiber, and may be chosen from, for example, hair, eyelashes, and eyebrows, as well as the stratum corneum of the skin and nails. The keratin fibers may include "living" hair, i.e. on a living body, or may be "non-living" i.e. in a wig, hairpiece or other aggregation of non-living fibers, such as used in textiles and fabrics. Mammalian hair, wool, fur and other melanin-containing fibers are suitable for use in the methods and with the compositions.

Not to be held to theory it is believed that the compositions of the current invention allow the colorant and/or color precursors to penetrate into the cortex layer of the keratin fiber to give semi-permanent or permanent coloration to the keratin fiber. As previously stated it has surprisingly been found that the color achieved closely approximates the original color of a person's hair. In many cases, the keratin fiber essentially returns to its original, natural color and shade.

The compositions of the present invention can comprise at least one catechol-based color precursor or a pharmaceutically acceptable salt thereof and at least one metal salt chosen from Fe(III), Fe(II), Co (II), Co(III), Ag(I), Ti(II), Cu(I), Cu(II), Cr(II), Cr(III), Mo(II), Mo(III), Ni(II), Ni(III), Mn(II) and Zn(II). The metals chosen are those metals which can act as a catalyst for the conversion of the color precursor to a colorant.

The anion of the salt may be a sulfate, halide, hydroxy carboxylate, phosphate or nitrate salt or a combination thereof. The anion can be one that allows the metal ion to dissolve in the pharmaceutically acceptable carrier, such as, for example, water.

The catechol-based color precursor is of the formula:

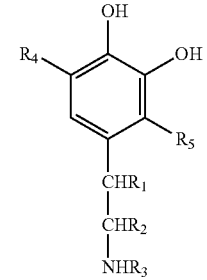

wherein $R_1$ and $R_2$ can be the same or different and are selected from the group consisting of H, alkyl of 1-6 carbons, $NH_2$, OH, silicon radicals, COOR' wherein R' is alkyl of 1-6 carbons or H, $CONH_2$, halogen, OR" wherein R" is alkyl of 1-6 carbons, $CH_2OH$, $CH_2NH_2$, and CONR'R" wherein R' and R" can be the same or different and are as defined above; $R_3$ is selected from the group consisting of H, alkyl of 1-6 carbons, and COR" wherein R" is as defined above; $R_4$ and $R_5$ can be the same or different and are selected from the group consisting of H, alkyl of 1-6 carbons, $NH_2$, OH, COOH, $CONH_2$, halogen, OR" wherein R" is as defined above, $NO_2$, $SO_3$, silicon radicals, HNR" wherein R" is as defined above, and NR'R" wherein R' and R" can be the same or different and are as defined above; or any pharmaceutically acceptable salts thereof or mixtures thereof.

An example of a catechol-based color precursor is L-DOPA, D-DOPA or pharmaceutically acceptable salts thereof and/or esters thereof or mixtures thereof.

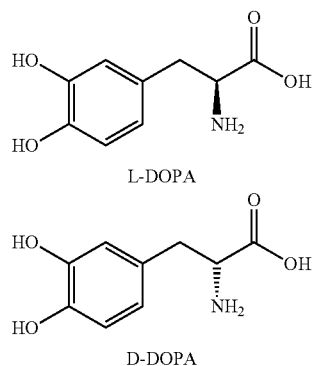

L-DOPA

D-DOPA

In the above embodiments, the catechol-based precursors can be the unsubstituted catechol compounds or they can have one or both of their phenolic hydroxy groups esterified to form pharmaceutically acceptable esters. The term catechol-based precursor is intended to mean either or both of the esterified or unesterified compound or compounds.

Without intending to be bound by theory, it is believed that esters of the catechol-based precursors of this invention can be used to slow the oxidation of the catechol-based precursor to allow sufficient time for diffusion into the hair cuticle. As used herein, the term "pharmaceutically acceptable ester" refers to esters which hydrolyze readily in situ and include those that break down readily within in the hair to leave the catechol-based precursor or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety has not more than 6 carbon atoms. Examples of particular esters include, but are not limited to, formates, acetates, propionates, butyrates, citrates, benzoates, lactates, acrylates and ethylsuccinates.

The compositions may further comprise a pharmaceutically acceptable base, such as, for example, a carbonate salt, a bicarbonate salt, an organic amine or combinations thereof. In an aspect, the pharmaceutically acceptable base is a sodium carbonate or a sodium bicarbonate.

In an aspect where both the pharmaceutically acceptable carbonate salt and a pharmaceutically acceptable bicarbonate salt are combined the mole ratio can be from about 0.05 to about 20. In a further embodiment the mole ratio can be about 0.5 to about 2.0. In a further embodiment, the mole ratio can be about 0.75 to about 1.5.

The compositions of the present invention may further comprise at least one oxidizing agent. The at least one oxidizing agent can be chosen from hydrogen peroxide, urea peroxide, alkali metal bromate, periodate, persulfate, perborate, iodate, peroxydisulfate, hypochlorite, ferric chloride, (2,2,6,6-Tetramethylpiperidin-1-yl)oxy, organic peroxides, tert-butyl hydrogen peroxide, cerium (IV) ammonium nitrate, and mixtures thereof.

In an aspect, the mole ratio of the oxidizing agent to the catechol-based color precursor may be, for example, greater than about 0.01 and less than about 2.0. Further, the mole ratio of the oxidizing agent to the catechol-based color precursor may be, for example, from about 0.1 to about 1.0. Still further, the mole ratio of the oxidizing agent to the catechol-based color precursor may be, for example, from about 0.2 to about 0.5.

In a further embodiment of the current disclosure, the composition of the present invention may be substantially free of aromatic diamines, organic solvents, organic co-solvents, and organic diluents or lead containing materials. In this embodiment the kit contains formulations which are essentially environmentally friendly.

Organic compounds such as the catechol-based precursor, described supra, may be synthesized in various solvents, co-solvents and diluents organic solvents, co-solvents and organic diluents and under various conditions. Accordingly, there may be residual solvents, co-solvents and diluents present as contaminants. Herein, the term "substantially free of" in reference to organic solvents, organic co-solvents and organic diluents, is intended to mean less than about 5% w/w of any of the compositions containing the catechol-based precursor.

The compositions may also further comprise at least one optional additive, such as, for example, thickening agents, abrasive material, wetting agents, surfactants, and cosmetically acceptable adjuncts, such as, for example, perfumes.

Surfactants useful in the compositions disclosed herein include, for example anionic, cationic, nonionic and amphoteric surfactants or their mixtures, for example, the alkylbenzenesulfonates, the alkylnaphthalenesulfonates, the sulfates, the ether sulfates and the sulfonates of fatty alcohols, the quaternary ammonium salts such as trimethylcetylammonium bromide and cetylpyridinium bromide; the ethanolamides of fatty acids optionally oxyethylenated; the polyoxyethylenated acids, alcohols or amines, the polyglycerolated alcohols, the polyoxyethylenated or polyglycerolated alkylphenols as well as the polyoxyethylenated alkylsulfates.

The quantities of surfactants present in the composition may vary from about 0.01 to about 40%, such as, for example, from about 0.5 to about 30% of the total weight of the composition.

The thickening agents that may be added to the compositions conforming to the invention may be selected from sodium alginate, gum arabic, cellulose and/or starch derivatives, acrylic acid polymers, cross-linked polyacrylate polymers and xanthan gum. It is also possible to use mineral thickening agents such as bentonite.

These thickening agents may be present in proportions from about 0.1 to 5%, for example, from about 0.2 to 3% by weight of the total weight of the composition.

The compositions may be free of chelating agents of the included metal salts used because these agents tend to reduce the catalytic capabilities of the metal ion for the oxidation of the oxidation dye precursors.

The compositions or various components of the composition of the disclosure may be coated with materials suitable for forming a controlled release matrix, prepared by known techniques, including microencapsulation, to delay adsorption of the dye or dye intermediates into the hair and thereby provide a sustained action over a longer period of time. For example, a material such as glyceryl monostearate or glyceryl distearate alone or with a wax may be employed as a material suitable for forming a controlled release matrix.

As further examples, an oligomer/polymer of hydroxyacetic acid and lactic acid or a oligomer/polymer of lactic acid and glycolic acid are suitable for use as an encapsulant material for controlled release of the oxidizing agent and can be used in conjunction with nonionic, cationic, anionic and zwitterionic surfactants from a melt or from admixture to produce the encapsulated oxidizing agent.

Encapsulated and microencapsulated oxidizing agents can be prepared by techniques known in the art; which techniques include, for example, pan coating, air suspension coating, centrifugal extrusion, core-shell encapsulation using a vibrational nozzle, spray drying, ionotropic gelation, coacervation, interfacial polycondensation, interfacial cross-linking, in-situ polymerization or matrix polymerization.

In a further aspect, the compositions of the current disclosure may also comprise one or more abrasive materials. Not to be held to theory, it is believed that the abrasive materials may aid in colorant or color precursor penetration into the keratin fiber by abrading a portion of any protective oils, waxes, or other natural or unnatural coatings or materials resident on the fiber. The abrasive may also act to open up the cuticular scale structure of the fiber to allow improved penetration of the colorant or color precursor.

The term "abrasive materials" means particles with a hardness that is greater than or equal to that of a particular keratin fiber to be colored. For example, the abrasive solid particles may have a hardness of 3 or more on the Mohs scale, 4 or more on the Mohs scale, or 5 or more on the Mohs scale depending on its ability to abrade a particular keratin fiber. The abrasive materials may be selected from inorganic and/or metallic particles such as, for example, boron nitride, aluminosilicate, zircon, silica, mixed aluminum oxides such as emery, zinc oxide, aluminum oxides such as aluminas or corundum, titanium oxide, mica titanium oxide, diatomaceous earth, carbides, silicon carbide or other metallic oxides, metals and metal alloys such as for example iron, steel, pearlite, silicates such as glass, quartz or sand, calcium carbonate, for example bora bora sand or Rose de Brignoles marble; or magnesium carbonate, pumice stone, amorphous silica, diamond, or ceramics. The abrasive materials may be selected from organic materials such as, for example, nutshell powders such as, for example, apricot or walnut, fruit kernels such as apricot, wood cellulose, for example ground bamboo, coconut shell, for example coconut exfoliator; polyamides, in particular Nylon-6; polyethylenes, polypropylenes and other organic polymeric materials. The abrasive materials may be a combination of both organic and inorganic materials.

The abrasive materials may have a flattened, spherical, elongate, polyhedral or irregular shape. The abrasive materials may range in size from microns to nanometers, depending on the specific keratin fiber to be colored.

The kits of the disclosure may take many forms. They may contain a plurality of packages each containing one or more ingredients. The packages useful for the current disclosure include, for example, plastic pouches, foil pouches, powders, aerosols, containers, sachets, pump systems, and solutions. The ingredients in the package may be as powders or in liquid form. The kit may contain more than one type of package, for example, the metal salt may be in solution in a container, while the catechol-based color agent may be packaged in a foil pouch.

As an example, the kit may contain a first package containing at least one oxidizing agent, a second package containing at least one catechol-based color precursor or a pharmaceutically acceptable salt thereof, and at least one pharmaceutically acceptable base, and a third package containing at least one metal salt chosen from Fe(III), Fe(II), Co (II), Co(III), Ag(I), Ti(II), Cu(I), Cu(II), Cr(II), Cr(III), Mo(II), Mo(III), Ni(II), Ni(III), Mn(II) and Zn(II) and a pharmaceutically acceptable base. The third package may contain a pharmaceutically acceptable base and a catechol-based color precursor. The third package may contain at least one metal salt chosen from Fe(III), Fe(II), Co (II), Co(III), Ag(I), Ti(II), Cu(I), Cu(II), Cr(II), Cr(III), Mo(II), Mo(III), Ni(II), Ni(III), Mn(II) and Zn(II), a pharmaceutically acceptable base and a catechol-based color precursor.

The above example may also include a fourth package or a fourth and a fifth package each containing at least one metal salt chosen from Fe(III), Fe(II), Co (II), Co(III), Ag(I), Ti(II), Cu(I), Cu(II), Cr(II), Cr(III), Mo(II), Mo(III), Ni(II), Ni(III), Mn(II) and Zn(II) which may be the same or different from metal salts in any of the first, second, or third packages.

In the above examples, each package may additionally include at least one thickening agent, at least one dispersing agent, at least one abrasive, and/or at least one wetting agent.

Any one of the packages of the above examples may contain ingredients in either a powder form or a liquid form.

The kit may provide sufficient materials for a single application or multiple applications.

Concentrations of the ingredients may vary depending on the specific application contemplated. In one example, whether in separate solutions or in one solution, the total molal concentration of the catechol-based precursor or its pharmaceutically acceptable ester or salt in water may be 0.01-2.0 mol/kg. In a further example, whether in separate solutions or in one solution, the total molal concentration of the catechol-based precursor or its pharmaceutically acceptable ester or salt in water may be 0.1-1.0 mol/kg. In a further example, whether in separate solutions or in one solution, the total molal concentration of the catechol-based precursor or its pharmaceutically acceptable ester or salt in water may be 0.15-0.5 mol/kg. In one example, whether in separate solutions or in one solution, the total molal concentration of the oxidizing agent in water may be 0.005-0.2 mol/kg. In a further example, whether in separate solutions or in one solution, the total molal concentration of the oxidizing agent in water may be 0.01-0.2 mol/kg. In a further example, whether in separate solutions or in one solution, the total molal concentration of the oxidizing agent in water may be 0.025-0.1 mol/kg.

The ratios of pharmaceutically acceptable base to metal salt is from about 233:1 to about 9:1. Other ratios may be used depending on the desired hair color and the amounts of the other components. The above ratios are suitable, for example, when the ratio of pharmaceutically acceptable base: catechol-based precursor: oxidizing agent is 6:3:1.

The ratio of pharmaceutically acceptable base to metal salt is from about 900:1 to about 100:1 when the catechol-based precursor: oxidizing agent: metal salt is 100:50:1.

When the ratio of pharmaceutically acceptable base: catechol-based precursor: metal salt is approximately 450: 100:1, the effective ratio of oxidizing agent to metal salt is from about 112:1 to about 25:1.

Ratios of metal salt to catechol-based precursor are generally from about 100:1 to about 7:1.

The final amount of pharmaceutically acceptable base that is used in the composition, either first or second, may need to be adjusted due to the multi-functional nature of the base. It aids in the oxidation, aids in buffering the solution keeping the pH relatively constant and it functions in aiding any thickening agent that depends on base to increase the formulation's viscosity.

A variety of ingredients may optionally be included in the formulations disclosed herein, or in one or more of the formulations in a kit, in order to impart desirable characteristics to the hair. For example, without limitation, embodiments may include additives such as humectants, moisturizers, proteins, vitamins, herbal extracts, color enhancers, plasticizers, color fixatives, additives that reduce static electricity build-up and fly-away, and the like. Further, specialty additives, may include alkalizers (e.g. urea), re-fatting agents (e.g., isopropyl myristate and palmitate, cetyl alcohol, propylene glycol), pearlescent agents (e.g., ethylene glycol distearate), dandruff control agents (e.g., zinc pyrithione); and conventional hair conditioning agents such as waxes, oils, stearalkonium chloride, dicetyldimonium chloride, stearamidopropyl dimethylamine, and other quaternary organic compounds.

Defoaming agents or defoamers may be desirable in controlling the physical properties of the formulations disclosed herein. Without limitation, these include Oil and wax based defoamers, powder defoamers, water based defoamers, silicone based defoamers, ethylene oxide/propylene oxide (EO/PO) based defoamers, alkyl polyacrylates and the like.

Non limiting examples of defoamers may include hydrogenated and non-hydrogenated vegetable oils extracted from plants, including coconut oil, corn oil, cottonseed oil, olive oil, palm oil, rapeseed oil, almond oil, cashew oil, hazelnut oil, macadamia oil, mongongo oil, pine nut oil, pistachio oil, walnut oil, bottle gourd oil, buffalo gourd oil, pumpkin seed oil, watermelon seed oil, acai oil, blackcurrant seed oil, borage seed oil, evening primrose oil, carob pod oil, amaranth oil, apricot oil, apple seed oil, argan oil, artichoke oil, avocado oil, babassu oil, ben oil, borneo tallow nut oil, cape chestnut oil, cocoa butter, algaroba oil, cocklebur oil, poppyseed oil, cohune oil, dika oil, false flax oil, flax seed oil, grape seed oil, hemp oil, kapok seed oil, lallemantia oil, manila oil, meadowfoam seed oil, mustard oil, nutmeg butter, nutmeg oil, okra seed oil (hibiscus seed oil), papaya seed oil, perilla seed oil, pequi oil, pine nut oil, poppyseed oil, prune kernel oil, quinoa oil, ramtil oil, rice bran oil, royle oil, sacha inchi oil, tea oil (camellia oil), thistle oil, tomato seed oil, and wheat germ oil, combinations thereof, and the like. Other defoamers may be used in the formulations disclosed herein. These include low-molecular-weight oligometric-type hydrophobic homo- and co-polymers made of ethers, vinyl ethers, esters, vinyl esters, ketones, vinylpyridine, vinypyrrolidone, fluorocarbons, amides and imides, vinyllidene chlorides, styrenes, carbonates, vinyl acetals and acrylics, combinations thereof, and the like.

Without intending to be bound by theory, upon mixing with aqueous solutions, the defoamer may form small droplets and spontaneously spread over aqueous films at the air/water interface of bubbles (part of the foam). The defoamer droplets quickly spread over the film layer and, coupled with strong de-wetting actions, thin out the film layer, causing the film to rupture. To facilitate such film rupture, micron-sized hydrophobic fumed silica particles may often be added to a defoamer formulation. Hydrophobic silica particles may congregate in the air/water interface along with the oil droplets. As the film layer thins out by spreading oil droplets, sharp irregular silica particles may help pierce the film and the foam as a whole. The combination of hydrophobic oil and solid silica particle may thus increase the overall defoaming potency. In embodiments, an anti-foam agent may include, for example, TEGO FOAMEX 830™, commercially available from Evonik Co, which includes mineral-oil with dispersed micron-sized silica particles having their surfaces modified with hydrophobic polyether molecules. In embodiments, the total weight of silica particles in the defoamer formulation may be less than about 3%. Both mineral oil and silica particles may help control foam formation. In addition, mineral oil may also be partially distilled out during the course of distillation, alleviating its potential impacts on toner particles. Such defoamers may potentially help suppress foaming and may permit a much more efficient solvent stripping in PIE by vacuum distillation. Accordingly, the overall distillation process may also proceed more calmly and cleanly without forming thick and long-life foams, reducing product loss due to foam boil-over and wall splashing.

The amount of defoamer present in the toner particles is from about 0.001 wt % to about 1.0 wt %, in embodiments, from about 0.01 wt % to about 0.6 wt %, in other embodiments, from about 0.05 wt % to about 0.3 wt %.

Antimicrobial or antifungal agents may be desirable in any of the packages described herein. Examples of antibacterial agents include, without limitation, chlorohexadiene gluconate, alcohol, benzalkonium chloride, benzethonium chloride, hydrogen peroxide, methylbenzethonium chloride, phenol, poloxamer 188, povidone-iodine, phenoxyethanol, glyceryl laurate, grapefruit seed extract, oregano oil cinnamon bark extract and mixtures thereof. Examples of antifungal agents include without limitation, miconazole nitrate, calcium undecylenate, undecylenic acid, zinc undecylenate, potassium sorbate and mixtures thereof.

There is also disclosed herein a process for coloring keratin fibers comprising applying to the keratin fibers a first composition, optionally rinsing the fibers, applying a second composition, and optionally rinsing and drying.

The first composition is obtained by combining two or more packages of the above kits in such a combination as to prepare an admix of at least one oxidizing agent, at least one catechol-based color precursor or a pharmaceutically acceptable salt thereof, and at least one pharmaceutically acceptable base. The first composition may further include at least one metal salt chosen from Fe(III), Fe(II), Co (II), Co(III), Ag(I), Ti(II), Cu(I), Cu(II), Cr(II), Cr(III), Mo(II), Mo(III), Ni(II), Ni(III), Mn(II) and Zn(II). The second composition is obtained by combining two or more packages of the above kits in such a combination as to prepare an admix of at least one oxidizing agent, at least one pharmaceutically acceptable base, and at least one metal salt chosen from Fe(III), Fe(II), Co (II), Co(III), Ag(I), Ti(II), Cu(I), Cu(II), Cr(II), Cr(III), Mo(II), Mo(III), Ni(II), Ni(III), Mn(II) and Zn(II).

The compositions and kits of the current disclosure, and the processes of using them on keratin fibers, allow the keratin fiber, such as for example, a person's hair to essentially return to its original, natural color and shade. It has surprisingly been found that when the "original" keratin fiber color is a light shade the above process is used. When the "original" keratin fiber color is a darker shade the below process is used.

In another process of the disclosure, the first composition is obtained by combining two or more packages of the above kits in such a combination as to prepare an admix of at least one oxidizing agent, at least one catechol-based color precursor or a pharmaceutically acceptable salt thereof, and at least one pharmaceutically acceptable base. The first composition may further include at least one metal salt chosen from Fe(III), Fe(II), Co (II), Co(III), Ag(I), Ti(II), Cu(I), Cu(II), Cr(II), Cr(III), Mo(II), Mo(III), Ni(II), Ni(III), Mn(II) and Zn(II). The second composition is obtained by combining two or more packages of the above kits in such a combination as to prepare an admix of at least one oxidizing agent, at least one catechol-based color precursor or a pharmaceutically acceptable salt thereof, at least one pharmaceutically acceptable base and at least one metal salt chosen from Fe(III), Fe(II), Co (II), Co(III), Ag(I), Ti(II), Cu(I), Cu(II), Cr(II), Cr(III), Mo(II), Mo(III), Ni(II), Ni(III), Mn(II) and Zn(II).

The above processes may include compositions that further contain at least one thickening agent, at least one dispersing agent, at least one abrasive, and/or at least one wetting agent.

It has been found advantageously that prophylactic treatment of growing hair, using the formulations and methods disclosed herein, tend to maintain uniform hair color without the appearance of gray hair growing near the skin. For example, depending on the rate of growth of the hair, repeated applications may be done every 5-30 days. As a further example, repeated applications may be done every 8-20 days. As a still further example, repeated applications may be done every 10-14 days.

It has been found, unexpectedly, that keratin fibers that have been weakened mechanically or embrittled by repeated shampooing, dirt or other caustic hair treatments may advantageously be strengthened by the coloring process disclosed herein, without using preparations containing, for example, dithiols. After treatment, the keratin fibers after the process show reduced brittleness and are mechanically stronger.

One of ordinary skill in the art may rinse and dry the keratin fibers before and after application of either the first and second compositions.

In an aspect, the keratin fibers are "virgin," i.e., they have never been subjected to a chemical treatment, such as coloring or straightening.

EXAMPLES

As used herein to describe "light" and "dark" coloration, standard hair color levels are used. The Standard Color Levels are defined on a scale of 1 to 10 with level 1 being the darkest, blackest color and level 10 being a very light blond color. Below are the 10 standard hair color levels:

Level 1: Black
Level 2: Darkest (almost black) Brown
Level 3: Very Dark Brown
Level 4: Dark Brown
Level 5: Brown
Level 6: Light Brown
Level 7: Dark Blond
Level 8: Medium Blond
Level 9: Blond
Level 10: Light Blond The lightest platinum blond colors are often referred to as level 11, 12, or even 13.

In post treatment 1, below, the ratio of carbonate to ferric ion is from about 11 to about 10:1 when the peroxide ion to ferric ion ratio is less than about 75:1.

The ratio of carbonate ion to peroxide is from about 0.5:1 to about 16:1. Catechol-based precursor to peroxide ratios are from about 20:1 to about 1:3. Altering these ratios allows for altering the amount of color formed during the processing.

The ratio of carbonate to catechol-based precursor was from about 0.5:1 to about 5:1.

Materials used in these examples were obtained from Aldrich Chemical Co. unless otherwise indicated. Percentages are wt/wt unless otherwise noted.

Example 1

Preparation and Application of Manganese-Catalyzed Keratin Fiber Treatment Formulation In a 1-oz wide-mouth polypropylene jar were combined 3,4-Dihydroxy-L-phenylalanine (0.18 g, 0.912 mmol) and sodium bicarbonate (0.165 g, 1.96 mmol). To this was added 0.810 mL of a 3 wt % aqueous solution of Carbopol 934 polymer. The mixture was stirred at room temperature with a spatula until homogenous. To the mixture was then added 0.090 mL of aqueous 0.0856 M manganese (II) catalyst solution (0.0077 mmol manganese, 5 mol % relative to hydrogen peroxide). (The manganese solution may be made from manganese sulfate, manganese chloride, or manganese gluconate). The mixture was again stirred until homogenous. Lastly, 3% hydrogen peroxide solution (0.175 mL, 0.156 mmol) was added to the mixture. Upon stirring, the development of a deep red color was observed. This red mixture was applied to a keratin fiber, in this example, a sample of 100% virgin white hair obtained from DeMeo Brothers, Inc, NJ (approximately 0.5 cm wide, 3 cm in length). The mixture was worked into the hair vigorously with a gloved finger. The sample was allowed to sit at room temperature for 30 to 40 minutes, during which time the hair turned dark brown to black in color. The sample was then thoroughly rinsed with warm water and allowed to dry, providing a uniform coloration of the hair.

Example 2

Preparation and Application of "Post-Treatment" Formulation

In a 1-oz wide-mouth polypropylene jar were combined 1.0 mL of a 6 wt % aqueous solution of hydrogen peroxide solution and 0.0297 g Carbopol 934 polymer. The mixture was stirred at room temperature with a spatula until homogenous. To the mixture was then added aqueous sodium carbonate solution (0.125 mL of a 9.57 wt % solution, 0.113 mmol). The mixture was again stirred until homogenous. Lastly, aqueous iron gluconate solution (0.125 mL of an 8.6 wt % solution, 0.046 mmol Fe) was added to the mixture. The mixture was stirred, and applied to the manganese-treated hair sample of Example 1. The mixture was worked into the hair vigorously with a gloved finger. The sample was allowed to sit at room temperature for 10 to 15 minutes. The sample was then thoroughly rinsed with warm water and allowed to dry to give a light hair coloration of 6 and above.

Example 3

Preparation and Application of "Post-Treatment" Formulation

In a 1-oz wide-mouth polypropylene jar were combined L-Dopa (0.0781 g, 0.396 mmol), sodium carbonate (0.0677 g, 0.639 mmol), and 1.25 mL of a 3 wt % aqueous solution of Carbopol 934 polymer. The mixture was stirred at room temperature with a spatula until homogenous. To the mixture was then added 3% aqueous hydrogen peroxide solution (0.391 mL). The mixture was again stirred until homogenous. Lastly, aqueous iron gluconate solution (0.056 mL of an 8.6 wt % solution, 0.021 mmol Fe) was added to the mixture. The mixture was stirred, and applied to the manganese-treated hair sample of Example 1. The mixture was worked into the hair vigorously with a gloved finger. The sample was allowed to sit at room temperature for 15 to 20 minutes. The sample was then thoroughly rinsed with warm water and allowed to dry to give a dark coloration of 5 and below.

Example 4

Alternate Preparations

Examples 1 through 3 were repeated but without the manganese ingredient in Example 1. The results were the same but the application time for the first application was 60-90 minutes.

Example 5

Preparation and Application of Manganese-Catalysed Hair Treatment Formulation Containing Abrasive To a bowl containing aqueous hydrogen peroxide solution (3%, 33.6 mL) and aqueous Carbopol 934 solution (3% by weight, 80 mL), diatomaceous earth (5.0 g) was added. The mixture was stirred until homogenous. To this mixture was added a powder mixture comprised of L-Dopa (17.28 g), sodium bicarbonate (15.84 g), and manganese gluconate (1.80 g). The mixture was again stirred until homogenous. As the mixture began to turn red, the material was applied generously to the hair of a person whose "original" hair color was a light brown, starting with the roots and temple areas. The formula was worked into the hair with a gloved hand, ensuring thorough coverage. The treatment was left on the hair at room temperature for 15 minutes. During this time, the mixture turned a dark brown to black in color. The material was then thoroughly rinsed from the hair with water. After post treatment 1, above, was then applied and the hair rinsed and dried, the color of the hair was rated as level 6.

While the processes as described are performed at room temperature they are also suitable for treatment at elevated temperatures by heating the combined contents of the two jars prior to application.

Again not to be held to theory it is believed that the application of the first formulation provides color to the cortex layer of the hair in a manner which "over" colors the hair. The application of the second formulation then removes excess colorant from the cortex allowing the "proper" amount of colorant to remain. The second formulation is formulated to be based on the original color of the hair. For example, Post Treatment 1 is designed for people whose original hair color was light (level 6 and higher), while Post Treatment 2 is designed for people whose original hair color was dark (level 5 and lower).

The present invention has been described in connection with various embodiments. Notwithstanding the foregoing, it should be understood that modifications, alterations, and additions can be made to the invention without departing from the scope of the invention as defined by the appended claims.

What is claimed is:

1. A kit for coloring keratin fibers comprising two or more packages, wherein the kit comprises:
    a. a package containing a first formulation, said first formulation comprising:
        i. one or more abrasive materials; and
        ii. optionally, an oxidizing agent
    b. one or more additional packages containing ingredients comprising: at least one catechol-based color precursor or a pharmaceutically acceptable salt thereof, at least one pharmaceutically acceptable base, at least one oxidizing agent, and at least one of a metal salt chosen from Fe(III), Fe(II), Co (II), Co(III), Ag(I), Ti(II), Cu(I), Cu(II), Cr(II), Cr(III), Mo(II), Mo(III), Ni(II), Ni(III), Mn(II) and Zn(II);
    wherein the first formulation does not contain a catechol-based color precursor, and wherein the ingredients are packaged separately or in combination, in various combinations of packages selected from the group consisting of powders, aerosols, distinct containers, sachets, pump systems, and solutions.

2. The kit of claim 1, wherein the first formulation further comprises one or more solution modifying ingredients selected from the group consisting of a thickener, a pharmaceutically acceptable carbonate or bicarbonate salt, and a surfactant.

3. The kit of claim 1, wherein the oxidizing agent is hydrogen peroxide.

4. The kit of claim 1, wherein the first formulation further comprises urea peroxide.

5. The kit of claim 1, further comprising a second package containing a colorant formulation, wherein the colorant formulation comprises the at least one catechol-based color precursor or a pharmaceutically acceptable salt thereof; at least one pharmaceutically acceptable base; and at least one oxidizing agent.

6. The kit of claim 5, further comprising a third package containing a post-treatment formulation, wherein the post-treatment formulation comprises: at least one pharmaceutically acceptable base; and at least one oxidizing agent.

7. The kit of claim 1, wherein the first formulation further comprises urea.

8. The kit of claim 1, wherein the first formulation or the ingredients in any of the additional packages further comprise a defoamer.

9. The kit of claim 1, wherein at least one of the additional packages further contains at least one thickening agent.

10. The kit of claim 1, wherein the catechol-based color precursor is of the formula:

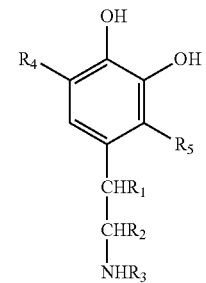

wherein $R_1$ and $R_2$ can be the same or different and are selected from the group consisting of H, alkyl of 1-6 carbons, $NH_2$, OH, silicon radicals, COOR' wherein R' is alkyl of 1-6 carbons or H, $CONH_2$, halogen, OR" wherein R" is alkyl of 1-6 carbons, $CH_2OH$, $CH_2NH_2$, and CONR'R" wherein R' and R" can be the same or different and are as defined above; $R_3$ is selected from the group consisting of H, alkyl of 1-6 carbons, and COR" wherein R" is as defined above; $R_4$ and $R_5$ can be the same or different and are selected from the group consisting of H, alkyl of 1-6 carbons, $NH_2$, OH, COOH, CONH$_2$, halogen, OR" wherein R" is as defined above, NO$_2$, SO$_3$, silicon radicals, HNR" wherein R" is as defined above, and NR'R" wherein R' and R" can be the same or different and are as defined above; or any pharmaceutically acceptable salts thereof or mixtures thereof.

11. A process for coloring keratin fibers using the kit of claim 1, comprising the steps of:
   a. treating the keratin fibers with the first formulation or a water dilution thereof; and
   b. applying the remaining contents of the kit to the hair.

12. The process for coloring keratin fibers of claim 11, further comprising the step of:
   c. rinsing the hair between process steps a and b.

13. The process for coloring keratin fibers of claim 11, wherein step b further comprises: prior to applying other ingredients to the keratin fibers, applying to the keratin fibers at least one of a metal salt chosen from Fe(III), Fe(II), Co (II), Co(III), Ag(I), Ti(II), Cu(I), Cu(II), Cr(II), Cr(III), Mo(II), Mo(III), Ni(II), Ni(III), Mn(II) and Zn(II).

14. The process for coloring keratin fibers of claim 11, wherein one of the additional packages comprises at least one pharmaceutically acceptable base and at least one catechol-based color precursor.

15. The process for coloring keratin fibers of claim 11, wherein one of the additional packages comprises at least one pharmaceutically acceptable base and at least one of a metal salt chosen from Fe(III), Fe(II), Co (II), Co(III), Ag(I), Ti(II), Cu(I), Cu(II), Cr(II), Cr(III), Mo(II), Mo(III), Ni(II), Ni(III), Mn(II) and Zn(II).

16. The process for coloring keratin fibers of claim 11, wherein the keratin fibers are mechanically weakened or brittle before the coloring process and whereby the keratin fibers after the process coloring is performed show reduced brittleness and are mechanically stronger.

17. A process for maintaining the color of growing keratin fibers comprising:
   ing the growing keratin fibers using the process of claim 10;
   b. repeating step a. every 10-14 days.

* * * * *